(12) United States Patent
Paschke

(10) Patent No.: US 8,629,088 B2
(45) Date of Patent: Jan. 14, 2014

(54) MIXTURE OF AT LEAST TWO FUSION PROTEINS, THE PRODUCTION THEREOF AND THE USE OF THE SAME

(75) Inventor: Matthias Paschke, Berlin (DE)

(73) Assignee: Scil Proteins GmbH, Halle (Saale) (DE)

( * ) Notice: Subject to any disclaimer, the term of this patent is extended or adjusted under 35 U.S.C. 154(b) by 0 days.

(21) Appl. No.: 13/222,272

(22) Filed: Aug. 31, 2011

(65) Prior Publication Data

US 2012/0015819 A1     Jan. 19, 2012

Related U.S. Application Data

(63) Continuation of application No. 10/537,588, filed as application No. PCT/EP03/13709 on Dec. 4, 2003, now abandoned.

(30) Foreign Application Priority Data

Dec. 4, 2002    (DE) .................................. 102 56 669

(51) Int. Cl.
| | |
|---|---|
| C40B 30/04 | (2006.01) |
| C40B 40/02 | (2006.01) |
| C12Q 1/70 | (2006.01) |
| C12Q 1/68 | (2006.01) |
| C12N 15/00 | (2006.01) |
| A61K 38/00 | (2006.01) |
| C07K 1/00 | (2006.01) |
| C07K 14/00 | (2006.01) |
| C07K 17/00 | (2006.01) |
| C40B 40/08 | (2006.01) |
| C12N 7/00 | (2006.01) |

(52) U.S. Cl.
USPC .......... 506/9; 506/4; 506/14; 506/17; 506/23; 435/5; 435/6.1; 435/69.7; 435/235.1; 435/320.1; 530/300; 530/350

(58) Field of Classification Search
USPC ............ 506/4, 9, 14, 17, 23; 435/5, 6.1, 69.7, 435/235.1, 320.1; 530/300, 350
See application file for complete search history.

(56) References Cited

U.S. PATENT DOCUMENTS

| 5,593,856 A | 1/1997 | Choi |
| 6,291,650 B1 | 9/2001 | Winter |

(Continued)

FOREIGN PATENT DOCUMENTS

| DE | 198 19 889 A1 | 11/1999 |
| WO | 92/18619 A | 10/1992 |

(Continued)

OTHER PUBLICATIONS

Jung et al. (Selection for improved protein stability by phage display, 1999, Journal of Molecular Biology, vol. 294, pp. 163-180).*

(Continued)

*Primary Examiner* — Sharmila G. Landau
*Assistant Examiner* — Shannon Janssen
(74) *Attorney, Agent, or Firm* — Rothwell, Figg, Ernst & Manbeck, P.C.

(57) ABSTRACT

The present invention concerns a protein mixture comprising at least a first fusion protein comprising a protein or protein fragment, and an interaction domain and a protein translocation sequence, which effects that the fusion protein upon expression in a bacterium is translocated through the cytoplasmic membrane in an essentially unfolded state and at least a second fusion protein comprising a protein or protein fragment, and an interaction domain and a protein translocation sequence which effects that the fusion protein is translocated through the cytoplasmic membrane upon expression in a bacterium in an essentially folded state, wherein the interaction domain of the first protein can bind to those of the second protein.

Tat dependent signal sequence

Figure 3:
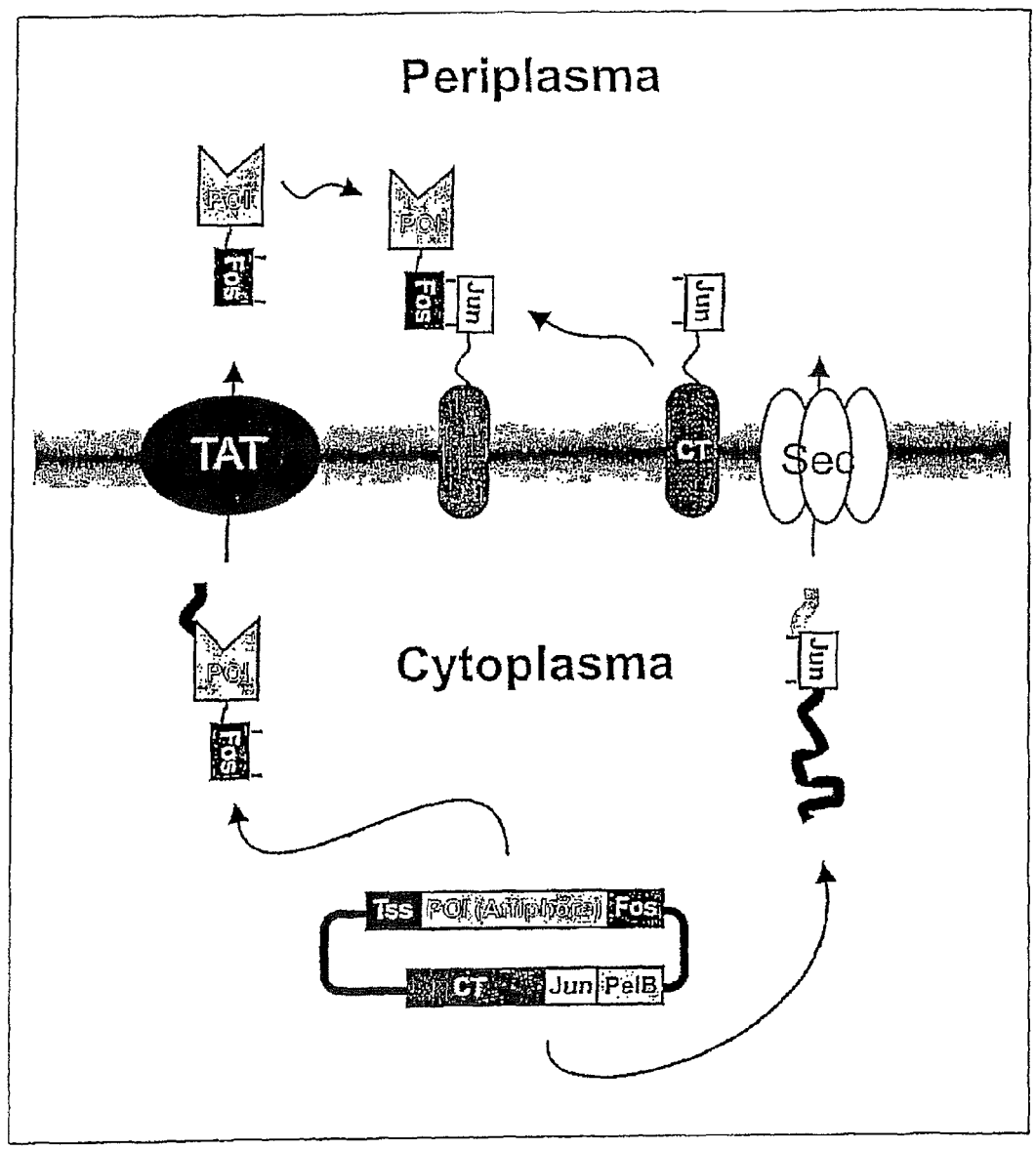

Sec, YidC and SRP dependent signal sequence

11 Claims, 8 Drawing Sheets

(56) References Cited

U.S. PATENT DOCUMENTS

| | | |
|---|---|---|
| 6,335,178 B1 | 1/2002 | Weiner |
| 7,419,783 B2 | 9/2008 | Georgiou |
| 2003/0219870 A1* | 11/2003 | Georgiou et al. ............ 435/69.1 |

FOREIGN PATENT DOCUMENTS

| | | |
|---|---|---|
| WO | 97/32017 A | 9/1997 |
| WO | WO 99/57314 A1 | 11/1999 |
| WO | 00/71694 A | 11/2000 |
| WO | 02/22667 A | 3/2002 |

OTHER PUBLICATIONS

Kremser et al. (The Adsorption Protein of Filamentous Phage fd: Assignment of Its Disulfide Bridges and Identification of the Domain Incorporated in the Coat, 1994, Biochemistry, vol. 33, pp. 13954-13958).*

Barth et al. (Compatible-Solute-Supported Periplasmic Expression of Functional Recombinant Proteins under Stress Conditions, 2000, Applied and Environmental Microbiology, vol. 66, pp. 1572-1579).*

K. Dane Wittrup, "Phage on display"; Tibtech, Nov. 1999 (vol. 17), pp. 423-424.

Crameri et al., "Display of Biologically Active Proteins on the Surface of Filamentous Phages: A cDNA Cloning System . . . ", Gene, vol. 137, 1993, pp. 69-75.

Delisa et al., "Genetic analysis of the twin arginine translocator secretion pathway in bacteria," Journal of Biological Chemistry, vol. 227, No. 33, Aug. 16, 2002, pp. 29825-29831.

Paschke et al., "New series of vectors for phage display and prokaryotic expression of proteins," Biotechniques, vol. 30, No. 4, Apr. 2001, pp. 720-726.

Dalbey et al., "Protein translocation into and across the bacterial plasma membrane and the plant thylakoid membrane," TIBS Trends in Biochemical Sciences, vol. 24, No. 1, Jan. 1999, pp. 17-22.

Settles et al., "Old and new pathways of protein export in chloroplasts and bacteria," Trends in Cell Biology, vol. 8, No. 12, Dec. 1998, pp. 494-501.

Samuelson et al., "YidC mediates membrane protein insertion in bacteria," Nature, Aug. 10, 2000, vol. 406, No. 6796, pp. 637-641.

Wu et al., membrane targeting and translocation of bacterial hydrogenases, 2000, Arch Microbiol, vol. 173, pp. 319-324.

Sanders et al., "Transport of cytochrome c derivatives by the bacterial Tat protein translocation system", Molecular Microbiology (2001) 41(1), 241-246.

de Kruif et al., "Leucine Zipper Dimerized Bivalent and Bispecific scFv Antigodies from a Semi-synthetic Antibody Phage Display Library", The Journal of Biological Chemistry, vol. 271, No. 13, Mar. 29, pp. 7630-7634, 1996.

Thomas et al., "Export of active green fluorescent protein to the periplasm by the twin-arginine translocase (Tat) pathway in *Escherichia coli*", Molecular Microbiology (2001) 39 (1), 47-53.

Rakonjac et al., "Filamentous Phage are Released from the Bacterial Membrane by a Two-step Mechanism Involving a Short C-terminal Fragment of pIII", J. Mol. Biol. (1999) 289, 1253-1265.

Marciano et al., "Assembling filamentous phage occlude pIV channels", PNAS, Jul. 31, 2001, vol. 98, No. 16, 9359-9364.

Gao et al., A method for the generation of combinatorial antibody libraries using pIX phage display, PNAS, Oct. 1, 2002, vol. 99, No. 20, 12612-12616.

Teter et al., "How to get a folded protein across a membrane", Cell Biology, vol. 9, Nov. 1999, 428-431.

Forrer et al., "Beyond binding: using phage display to select for structure, folding and enzymatic activity in proteins", Curr. Op. in Structural Biology, 1999, 9; 514-520.

Berks et al., "The Tat protein export pathway", Molecular Microbiology, (2000), 35(2), 260-274.

Robinson et al., "Protein Targeting by the Twin-Arginine Translocation Pathway", Molecular Cell Biology, vol. 2, May 2001, 350-356.

Santini et al., "Translocation of Jellyfish Green Fluorescent Protein via the Tat System of *Escherichia coli* and Change of its Periplasmic . . . ", The Journal of Biological Chemistry, vol. 276, No. 11, Mar. 16, pp. 8159-8164, 2001.

Gao et al., "Making artificial antibodies: A format for phage display of combinatorial heterodimeric arrays", Proc. Natl. Acad. Sci. USA, vol. 96, pp. 6025-6030, May 1999.

K. Dane Wittrup, "Phage on display", Tibtech, Nov. 1999, vol. 17, pp. 423-424.

* cited by examiner

Fig. 1
Tat dependent signal sequence
←——————— about 18-26 ———————→
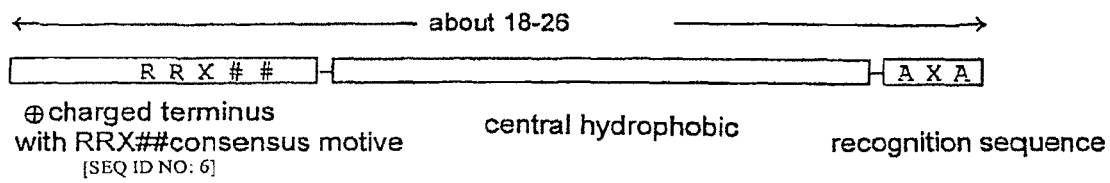
⊕ charged terminus
with RRX##consensus motive
[SEQ ID NO: 6]
central hydrophobic
recognition sequence
Sec, YidC and SRP dependent signal sequence
←——————— about 26-58 ———————→
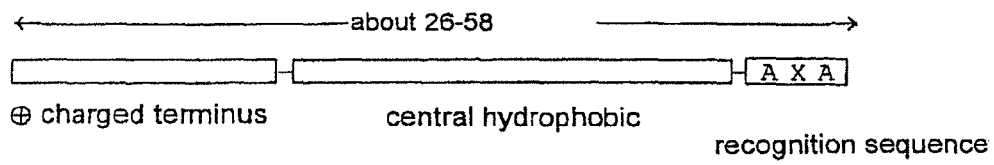
⊕ charged terminus    central hydrophobic
recognition sequence

Fig. 2

```
M   N   N    N   D   L    F   Q   A  R   R   R   F   IA   Q   L   G    G   L   T
ATGAACA  ATAACGATCT  CTTTCAGGCA  TCACGTCTTTCTGGC  ACAACTCGGC  [SEQ ID NO: 8]
TACTTGT  TATTGCTAGA  GAAAGTCCGT  AGTGCAGAAAGACCG  TGTTGAGCCG  [SEQ ID NO: 9]
```

```
                              | R  R  X  #  # |—
⊕ charged N-terminus   RRX##consensus motive    central hydrophobic
                           [SEQ ID NO: 6]
```

```
V   A   G   M    L   G   P    S   L   L   TR   R   A   T   A  [SEQ ID NO: 7]
GTCGCCGGGAT  GCTGGGGCCGATTGTTAA  CGCCGCGACG  [SEQ ID NO: 10]
CACCGCCCTA  CGACCCCGGC  AGTAACAATGCGCTGC  [SEQ ID NO: 11]
```

```
——————————————————————————————————————— | A  X  A |
        central hydrophobic               leader peptidase
                                          recognition sequence
```

MIXTURE OF AT LEAST TWO FUSION PROTEINS, THE PRODUCTION THEREOF AND THE USE OF THE SAME

This application is a continuation of U.S. Ser. No. 10/537,588 filed on Sep. 2, 2005, which is a 35 U.S.C. 371 National Phase Entry Application from PCT/EP2003/013709, filed Dec. 4, 2003, which claims the benefit of German Patent Application No. 102 566 69.0-41 filed on Dec. 4, 2002, the disclosures of which are incorporated herein its entirety by reference.

The present invention concerns a protein mixture comprising at least a first fusion protein comprising a protein or protein fragment, and an interaction domain and a protein translocation sequence, which effects that the fusion protein upon expression in a bacterium is translocated through the cytoplasmic membrane in an essentially unfolded state and at least a second fusion protein comprising a protein or protein fragment, and an interaction domain and a protein translocation sequence which effects that the fusion protein is translocated through the cytoplasmic membrane upon expression in a bacterium in an essentially folded state, wherein the interaction domain of the first protein can bind to those of the second protein.

Phage display technology is currently used in many areas of biotechnology for identifying proteins with desired properties and enzymatic activities (Forrer, P. et al. (1999) Current Opinion in Struct. Biol. 9:514-520 and Gao, C. et al., (2002) Proc. Natl. Acad. Sci. U.S.A. 99:12612-12616). Similarly, the technology is used to improve, for example, binding properties, the encymatic properties and/or the thermodynamic stability of proteins already known or isolated by phage display technology (Forrer, P. et al. (1999) supra). The basis for the phage display technology lies in the observation that certain so called non-lytic bacteriophage merely infect bacteria and that the phage particles are not released by lysis of the bacterium but rather that the individual parts of the bacteriophage are transported through the cytoplasma into the periplasma and eventually to the bacterial cell surface where the complete phage is assembled which eventually disengages from the bacterial cell. The fusion of the protein of interest with a phage coat protein thus leads to the export of this protein from the bacterial cytoplasma and the presentation on the surface of the bacterium. Phage coat proteins suitable for presentation are for example pIII, pVI, pVII, pVIII and pIX derived from M13 phagemid (Gao, C. et al. (2002) supra).

The N-terminus of the phage coat protein is oriented towards the outside and, consequently, the fused protein has to be arranged N-terminally of the phage coat protein in order for it to be presented on the surface. This does not represent a problem, if single already known proteins are fused with one of the indicated phage coat proteins since the START and STOP codons of these proteins are known. It, however, leads to problems if a so called phage library has to be created wherein the phage coat proteins are fused with a cDNA library. The problem is caused by the fact that the coding nucleic acids comprised in the cDNA library usually comprise translational STOP codons at the 3'-end since the cDNAs resulting from poly($A^+$) selection of the mRNA and from subsequent oligo-(dT)-priming always comprise translational STOP codons. Thus, a STOP codon will always be located between the cDNA and the phage coat protein upon fusion of an oligo-(dT)-primed cDNA 5' of the phage coat protein which in turn will inhibit expression of a fusion protein consisting of the cDNA encoded protein and the phage coat protein. Thus, Crameri, R. and Suter, M. (1993) Gene 137:69-75 developed a novel cloning and expression system based on the fact that the interaction domains of the two oncoproteins cJun and cFos were used, which form through a protein motive of regularly spaced leucine residues the so called "leucine zipper", a strong interaction between the two proteins (Landschulz et al. (1988) Science 240:1759-64) to connect the respective separately expressed phage coat protein and the cDNA encoded protein to form a heterodimer. For that purpose a fusion protein was expressed directed by a LacZ promoter which consisted of cJun and a C-terminus and of a phage coat protein (pIII) and, a second fusion protein which consisted of cFos at its N-terminus and of a cDNA library at its C-terminus, wherein also this protein was driven by a second LacZ promoter. Through the interaction between cJun and cFos via the respective leucine zipper within the periplasma of a bacterium the presentation of proteins and protein fragments, respectively, encoded by cDNAs became possible on filamentous phage.

When using the phage display technology there is the further problem that the assembly of the phage and, thus, the incorporation of the fusion proteins into the phage particles is carried out only in the periplasma (Russel et al. (1997) Gene 192(1):23-32). To export the respective fusion proteins into the periplasma of the bacterial cell an Sec signal sequence has to be added to the fusion protein by gene technological methods where applicable. This signal sequence causes the fusion protein to be transported in an essentially unfolded state into the periplasma. A large number of proteins, however, cannot be transported into the periplasma through the Sec transport pathway because the transport is inhibited by so called "stop-transfer" sequences or because of too rapid folding of the protein which occurs already in the cytoplasma. Stop-transfer sequences cause through the localized accumulation of positively charged amino acids in the protein sequence that the respective protein becomes stuck in the membrane upon translocation by the Sec transport pathway. Proteins which due to their rapid and/or stable folding cannot be bound in its unfolded form by proteins of the Sec transport pathway, in particular by SecB, are not transported through the Sec translocase complex and remain in the cytoplasma (Yamana et al. (1988) J. Bio. Chem. 263:19690-19696 and Berks, B. C. (1996) Mol. Microbiol. 22:393-404 and Bergs, B. C. et al. (2000) Mol. Microbiol. 35:260-274). Proteins dependent on reducing conditions or which depend for their function on cytoplasmic co-factors like, for example, FeS centres or molybdopterin can also not reach the periplasma via the Sec transport pathway in functional form. Accordingly, many polypeptides due to the lack of compatibility with the Sec transport pathway cannot be presented in a functionally folded state by phage display and subsequently be selected. The translocation of fusion proteins through the Sec transport pathway into the periplasma, thus, represents a significant disadvantage of the phage display techniques known in the prior art.

From the different requirements on the cellular conditions for folding of certain proteins a further problem arises upon expression of fusion proteins, in particular in bacteria if one part of the fusion protein only attains a correct folding in the periplasma as is the case, for example, with antibody proteins (Gao, C. et al. (2002) supra) and the other part of the fusion protein can only be correctly folded in the cytoplasma as is the case, for example for green fluorescent proteins (GFP) which is incompatible with Sec. Thus, the expression of, for example antibody-GFP-fusion proteins, i.e. fluorescently tagged antibody molecules is currently not possible in bacteria. The limitation to the Sec transport pathway, thus, prevents the production of a number of interesting protein conjugates, in particular in bacteria.

One object of the present invention is, thus, to overcome the limitation of the phage display technology of the prior art and to allow the production of fusion proteins which do not yield functional fusion proteins when produced by the prior art methods.

Thus, the present invention in one aspect provides a protein mixture comprising: a) at least a first fusion protein comprising: i) a protein or protein fragment, ii) an interaction domain and iii) a protein translocation sequence which effects that the fusion protein upon expression in a bacterium is translocated through the cytoplasmic membrane in an essentially unfolded state and b) at least a second fusion protein comprising i) a protein or protein fragment, ii) an interaction domain and iii) a protein translocation sequence which effects that the fusion protein upon expression in a bacterium is translocated through the cytoplasmic membrane in an essentially folded state, wherein the interaction domain of the first fusion protein can bind to those of the second fusion protein.

The protein or protein fragment of the first fusion protein comprises preferably proteins, which are translocated through the cytoplasmic membrane of the bacterium, preferably a Gram negative bacterium in an unfolded state and which accordingly do not require the reducing cytoplasmic environment and/or cytoplasmic co-factors for correct folding and which can also attain an essentially correct folding in periplasma. Examples of such proteins comprise but are not limited to the immune globulin heavy chains, immune globulin light chains, fragments of these chains, so called "single-chain-antibody" (Bird, R. E. (1988) Science 242:423-6), diabodies (Holliger, P. (1993) Proc. Natl. Acad. Sci. 90(14): 6444-8) receptors preferably extracellular domains of receptors like, for example, EGFR, PDGFR or VEGFR or receptor ligands like, for example, EGF, PDGF, or VEGF, integrines, preferably their extracellular domains, intimines and their domains, like for example EaeA, carbohydrate binding proteins and domains thereof like, for example, MBP and CBD, album binding proteins and domains or protein A and its domains.

The protein or protein fragment of the second fusion protein can be any protein or protein fragment preferred are, however, protein fragments which attain their folding and/or their function only if they are folded in the cytoplasma of a bacterium and which are thus translocated through the cytoplasmic membrane into the periplasma in an essentially folded state. Examples of such proteins are autofluorescent proteins like, for example, GFP or variants thereof with altered absorption maxima, enzymes like, for example, β-lactamase, co-factor dependent proteins like, for example, TMAO reductase and horseradish peroxidase, proteins which are encoded by a cDNA derived from a cDNA library or synthetic proteins.

In a preferred embodiment the protein or protein fragment of the first fusion protein and the protein translocation sequence is a phage coat protein or a periplasmatic marker enzyme, like PhoA, an intimin, a protein of the outer bacterial membrane or a periplasmatic receptor protein, in particular a carbohydrate binding protein. Preferred phage coat proteins which can be comprised in a protein mixture of the present invention are selected from M13 phagemid coat proteins pIII, pVI, pVII, pVIII and pIX. Out of these phage coat proteins only pIII and pVIII are provided with a known Sec dependent protein translocation sequence while the protein translocation sequences comprised in the remaining phage coat proteins have not been identified as of yet. Since these phage coat proteins are transported into the periplasma of the bacteria in an essentially unfolded state such proteins are considered as proteins which consist of a protein or protein fragment and a protein translocation sequence within the meaning of the invention without identification of the protein translocation sequence.

The interaction domains which are used in the first and the second fusion protein lead to binding of the first fusion protein to the second fusion protein. Thereby interaction domains are preferred which result in a relatively stable interaction between the two proteins, wherein a relatively stable interaction is an interaction which remains stable in the oxidative environment of the periplasma, on the bacterial cell surface or also outside the cell upon secretion of the heterodimer or heteromultimer. Suitable interaction domains of the first and second fusion protein which can be comprised in the fusion protein according to the invention are, for example, a leucine zipper domain and a leucine zipper domain as they have been described for the first time in the two oncoproteins cJun and cFos (Landschulz et al. (1988) supra) or variants thereof derived from other hetero- or homodimers as well as artificial leucine zipper domains or helix-loop-helix-domains and helix-loop-helix-domains (Moor et al. (1989) Cell 56:777-783), a calmodulin and a calmodulin binding peptide (Montigiani, S. et al. (1996) JMB 258:6-13) or in each case of a peptide of a peptide dimer. The term interaction domain also comprises domains which allow the formation of multimers of more than two fusion proteins.

The protein translocation sequence of the first fusion protein effects that the fusion protein is translocated upon expression in a bacterium preferably in a Gram negative bacterium through the cytoplasmic membrane into the periplasma in an essentially unfolded state. Someone of skill in the art is capable of identifying suitable protein translocation sequences without undue burden by utilizing the following experiments. A protein sequence potentially suitable as protein translocation sequence, which leads to the translocation of a protein fused therewith in an essentially unfolded state, is used with a protein comprising a GFP-myc-TAG. If the potential protein translocation sequence does not lead to protein translocation into the periplasma the GFP protein is formed in the cytoplasma of the bacterium which can be detected via the cytoplasmic fluorescence. In this case it does not reach the surface or the media and, thus, the myc-TAG can neither be detected in the medium nor on the surface with an anti-myc-antibody, like for example the monoclonal antibody 9E10. If the sequence leads to translocation of the fusion protein into the periplasma and eventually to the presentation on the surface and secretion into the environment of the bacterium, respectively, the presented and secreted, respectively, GFP-myc-TAG fusion protein can be detected through an anti-myc-antibody in the medium and/or on the surface of the bacterium. At the same time no fluorescence should be detectable in the periplasma since upon translocation of the GFP into periplasma in an essentially unfolded state the protein will not be folded correctly (so called "Sec-incompatibility"). The protein translocation sequences which are preferably used in the first fusion protein are those which are recognized in the Sec dependent transport pathway (Danese, P. N. and Silhavy, T. J. (1998) Annu. Rev. Genet. 32:59-94) in the SRP dependent transport pathway (Meyer, D. I. et al. (1982) Nature 297:647-650) or in the YidC dependent transport pathway (Samuelson, J. C. et al. (2000) Nature 406:637-641). However, it can also be a transport pathway independent sequence. Particularly suitable folding protein translocation sequences are, for example, signal sequences of PhoA, PelB, OmpA and pIII.

As a further element the second fusion protein comprises a protein translocation sequence which effects that the fusion protein is translocated through the cytoplasmic membrane upon expression in a bacterium, preferably in a Gram negative bacterium in an essentially folded state. A protein translocation sequence with this property is present, if a protein, for example, GFP which can only attain its functional confirmation in the cytoplasma of a bacterium, is transport into the periplasma without a loss of auto fluorescence. This property of the protein translocation sequence of the invention can be assessed with the experiment described above with respect to the first protein translocation sequence. With a similar experiment the consensus motive for the Tat specific leader peptide of the twin-argenine translocation (Tat) transport pathway of bacteria and plant chloroplasts have been determined. The Tat transport pathway known in the art allows the transport of proteins already folded in the cytoplasma into the periplasma and, thus, the transport of proteins into the periplasma which are incompatible with the Sec transport pathway. Similar to the transport through the Sec transport pathway also the Tat transport is mediated by a specific group of leader sequences (DeLisa, M. P. et al. (2002) J. Biol. Chem. 277:29825-29831). A further transport pathway known in the art which allows the transport of proteins in an essentially folded state is the one via thylakoid membranes (Settles, A. M. and Martienssen, R. (1998) Transcell Biol. 8:494-501). Accordingly, the second fusion protein comprises in a preferred embodiment of the present invention a signal sequence which is recognized by the Tat dependent transport pathway or by a thylakoid-Δ-ph dependent transport pathway and which, thus, leads to translocation of the fusion protein in an essentially folded state. A consensus motive of a protein translocation sequence recognized by the Tat dependent transport pathway is described in DeLisa, M. P. et al. ((2002) supra). The sequence is: S/T/RRXFLK.

In a preferred embodiment of the protein mixture of the present invention at least a first and at least a second fusion protein are covalently or non-covalently bound to each other. To attain a covalent bond between the two separately expressed fusion proteins it is possible to additionally place cystein residues or homologes thereof within the protein in the vicinity of the interaction domain, which will create a covalent bond between the two fusion proteins in the oxidative environment of the periplasma. Covalent bond can, for example, also be effected by the incorporation of amino acids with photoactivatable groups in both fusion proteins and subsequent UV-exposure of the proteins which are initially only bond to each other non-covalently. Someone of skill in the art is aware of further methods to bind together to proteins, which are initially only bound together by non-covalent bonds. Methods known to a skilled person in order to covalently bind two fusion proteins which are non-covalently bound comprises, for example, psoralen crosslinking.

A further aspect of the present invention is a nucleic acid mixture which encodes a protein mixture of the present invention. A coding nucleic acid within the meaning of the present invention is a nucleic acid sequence which encodes a polypeptide of the invention or a precursor thereof. Preferably, the nucleic acid mixture is DNA or RNA, preferably a DNA, wherein the DNA can be single stranded or double stranded. The nucleic acid respectively encoding the first or the second fusion protein furthermore comprises promoters which allow the expression of the respective fusion proteins in the host cell. Suitable promoters for the expression in, for example, *E. coli*, are the trp promoter, lacZ promoter, tet promoter, T7 promoter or ara promoter. Further elements which can be present in the nucleic acids, which constitute the respective nucleic acid mixture, are origins of replication (Ori), selective marker genes which, for example, mediate ampicilin or chloramphenicole resistance. Aside from the region coding for the respective fusion proteins the nucleic acids can comprise those elements, which are usually employed in bacterial expression vectors. Someone of skill in the art is aware of a number of such elements as well as vectors like for example pGEM or pUC.

In a preferred embodiment of the nucleic acid mixture of the present invention the two nucleic acids coding for the first and the second fusion protein are covalently linked to each other, preferably via phosphor diester bond. In particular the nucleic acid molecules which code for the first and the second fusion protein and which comprise suitable regulatory elements are comprised on one plasmid, thus, allowing that the protein mixtures according to the invention can be prepared, for example, in a bacterium already by transfection of only one plasmid and by infection with only one phage, respectively, if the nucleic acid is comprised in a phage. In a preferred embodiment both fusion proteins are expressed under the control of only one promoter as bicistronic cassette.

A further aspect of the present invention is a vector comprising a protein mixture of the invention and/or comprising a nucleic acid mixture of the invention. A vector within the meaning of the invention is a protein-nucleic acid mixture, which is capable to introduce the protein mixtures and/or nucleic acid mixtures comprised therein into a cell. In that it is preferred that the fusion proteins encoded by the nucleic acid mixtures are expressed in the cells and that de novo synthesized fusion proteins can be recovered from the cells and can be presented on the cell surface, respectively. Suitable vectors are, for example non-lytic phages, like M13 phage, fd phage, F1 phage and lytic phage, like λ phage.

A further aspect of the further invention is a cell comprising a protein mixture of the invention, a nucleic acid mixture of the invention and/or a vector of the invention. Cells of the invention can be prokaryotic or eukaryotic cells. In the preferred embodiment of the present invention the cells of the invention are prokaryotic cells, in particular bacteria and more preferably *E. coli* (TG1, XL-1, JM83, BL21) or *B. subtilis*.

A further aspect of the present invention is a library comprising at least two protein mixtures of the present invention, at least two vectors of the present invention and/or at least two cells of the present invention, wherein the proteins or protein fragments of the respective first or the respective second fusion protein are different from each other. Such a library can either comprise specifically selected different known proteins or protein fragments or the interaction domain and the protein translocation sequence on the first or the second, preferably the second fusion protein can be fused with a cDNA library, wherein the expression of these nucleic acids leads to a number of different first or second fusion proteins which respectively comprise different proteins or protein fragments. Preferably the cDNA part is expressed at the C-terminus of the fusion protein to thereby circumvent the previously described problem with N-terminal fusion of a cDNA. In a preferred embodiment the library comprises a large number of cells of the present invention when each cell produces a different protein mixture, preferably presents it on its surface. In case that the protein or protein fragment and interaction domain of the first protein is a phage co-protein the library of the present invention allows the presentation of a large number of proteins or protein fragments, which are comprised in the second fusion protein. The presentation is, thus, not limited as are the phage display libraries known in the prior art to proteins or protein fragments which fold into their functional form in the periplasma of the cell but also comprises proteins which can attain the functional folding in the cytoplasma.

The protein mixtures according to the invention which can form heterodimers or multimeres, wherein the components of the heterodimers or multimeres attain their three dimensional structure in at least two different cellular compartments can now be used in a number of methods comprising among others phage display.

A further aspect of the present invention is, thus, a method for identifying substances which can bind to a protein mixture, a vector of the present invention or to a cell of the present invention comprising the step:
  a) contacting at least one potential binding substance with a protein mixture of the invention, a vector of the invention or a cell of the invention and
  b) determining the binding of the substance to said protein mixture, said vector and/or said cell.

This method primarily serves the purpose of identifying a substance or substances, which can bind to an already known protein target, for example, to identify an inhibitor, an activator, competitor or modulator of the known protein target. The potentially binding substances the binding of which to a protein mixture of the invention, a vector of the invention and/or the cell of the invention should be measured can be any chemical substance or substance mixture. For example, it can be substances from a peptide library, substances from a combinatorial chemical library, cell extracts, in particular plant cell extracts and proteins or protein fragments.

Contacting of the potentially binding substance(s) with a protein mixture, vector or cell of the invention is understood to mean any possibility of interaction between the two components wherein both components can be independently of each other in liquid phase, for example, in solution or in suspension, or can be attached to a solid phase, for example, to an essentially planar surface or can be in the form of particles, pearls or the like. In a preferred embodiment there is a plurality of different potentially binding substances immobilized on a solid surface and is contacted with the protein mixture of the invention, a vector of the invention or cells of the invention and subsequently binding of the substances of the invention to the various positions at which the respective different potentially binding substances are immobilized is measured.

Measuring of binding of the protein mixtures, the vectors or the cells of the present invention to potentially binding substances can be carried out by measuring a marker connected to the protein mixture of the invention, the vector of the invention or the cell of the invention wherein suitable markers are known to the person skilled in the art and comprise, for example, fluorescence or radioactive markers. In a preferred embodiment the protein mixture, the vector, or the cell comprises in addition to the second fusion protein beside the protein or protein fragment the interaction of which with the potentially binding substance is to be investigated, an autofluorescent protein like, for example, GFP or variants thereof. Measuring the binding of the substance can also be detected via the change of electrochemical, in particular redox properties of, for example, the immobilized potentially binding substances after contacting. Suitable methods comprise, for example, potentiometric methods. Further methods for detecting the binding of two molecules or molecular mixtures are known to someone of skill in the art and can all equally be employed for measuring the binding of the potentially binding substance to the protein mixture of the invention, the vector of invention or the cells of the invention.

If needed it is possible to introduce further steps prior to, in between or after the steps of the method of the invention like, for example, one or several washs after contacting to remove, for example, non-specific bonds between the potential binding substance and the protein mixture of the invention, the vector of the invention or the cell of the invention.

As a further step after measuring the binding of the substance the binding substance can be selected on the basis of, for example, the strength of the bond and can then be used directly, for example, for the inhibition of the known protein target. It is, however, also possible to modify the binding substance by methods known in the art which also comprise methods of combinatorial chemistry. For example, by adding halogen side groups, preferably F or Cl, by adding lower alkyl groups like methyl, ethyl, n-propyl, iso-propyl, n-butyl, iso-butyl or tert-butyl groups or by adding amino, nitro, hydroxyl, amido, or carboxylic acid groups. The thus differently modified binding substances can then again be tested for the binding in the method of the invention and can be optimized with respect to the desired binding specificity and the effect caused thereby (for example, activation, inhibition or modulation of the respective activity).

A further aspect of the present invention is a method of identifying proteins or protein fragments, which bind to a test substance comprising the steps:
  a) contacting at least one test substance with a library of the present invention and
  b) measuring the respective binding of the test substance to the different protein mixtures, vectors and/or cells of the library of the present invention.

In this method protein or protein fragments are selected which can bind to a given test substance. Preferably those are proteins or protein fragments of the second fusion proteins, since this is correctly folded with a higher probability as compared to the proteins or protein fragments of the first fusion proteins which are only correctly folded, if the respective proteins can also attain their native conformation in the oxidative environment of the periplasm. A test substance within the meaning of the present invention can be any chemical substance or a mixture thereof. Preferably it is a protein or protein fragment, in particular a receptor or receptor ligand, a transcription factor, an ion channel, a molecule of the signal transduction cascade, a structure or storage protein, a toxin, a light receptor protein and pigment protein. Measuring of the respective binding of the various protein mixtures, vectors and/or cells of the library to the test substance can be carried out as described above via marker dependent or marker independent assay methods.

In a preferred embodiment the method of the present invention comprises the further steps: Selecting at least one protein mix, one vector or one cell based on the measured binding and producing a second library wherein the library is produced by modification of the protein or protein fragment, which is comprised in the selected protein mix, in the selected vector or in the selected cell. The selection process of protein mixtures, vector or cells from the library is preferably carried out on the basis of the strength of the bond wherein protein mixtures, vectors or cells are preferred which show the strongest binding to the respective test substance. Starting from the amino acid sequence of the protein or protein fragment comprised in the selected protein mixture, vector or cell, which can be determined by standard methods, modification can be generated which respectively lead to minor changes in the amino acid sequence and thus to a multitude of derivates which show a slightly different three dimensional structure in comparison to the starting protein and protein fragment, respectively. Such modifications can be obtained using methods known in the art like, for example, by random mutagenesis or by targeted substitution of single nucleic acid codons of the nucleic acid coding for the protein or protein fragment. It is thereby preferred that substitutions are so called "conservative" substitutions. A conservative substitution is present if, for example, a nucleic acid codon coding for a basic amino acid is replaced by another nucleic acid codon coding for a basic amino acid, a nucleic acid codon coding for another acidic amino acid is replaced by a nucleic acid codon, coding for a acidic amino acid and a nucleic acid codon coding for a polar amino acid is replaced by another nucleic acid codon coding for a polar amino acid, respectively.

The second library newly generated on the basis of the selected protein mixtures, vectors or cells can now again be contacted in a further step with the test substance whereupon in a further step the respective binding of the test substance to the modified protein mixtures, vectors or cells of the second library is measured. As the case may be it is now possible to repeat the steps of selecting at least one protein mixture, at least one vector or at least one cell on the basis of the measured binding and the subsequent production of a third and n-fold, respectively library as well as the contacting and measuring of the respective binding of the test substance to the various protein mixtures, vectors or cells of the third and n-fold library for one to n-fold times until a protein mixture, a vector or cell is selected which shows the desired binding.

The previously described method is also termed directed evolution since in a multitude of steps, which consist of modification and selection, proteins or protein fragments are further developed with respect to particular property in particular the binding property in an "evolutionary" way.

The proteins or protein fragments which have been identified or additionally have been optimized with respect to a particular property by above method can now be used as an active agent in a medicament, if they have been, for example, optimized for activation or repression of a particular cellular signal pathway. The same applies to binding substances which have been identified in methods for determining potentially binding substances. Thus, the methods of the present invention comprise in a preferred embodiment the further step that the selected binding substance or the protein or protein fragment or a variant thereof comprised in the selected protein mix, in the selected vector or in the selected cell is admixed with a pharmaceutical acceptable carrier and/or auxiliary substance.

A "variant" of the protein or protein fragment comprises modifications of the N- or C-terminal or modification of amino acid side chains which, for example, increase the stability, solubility or biocompatibility of the proteins or protein fragments. Also comprised are fusion proteins of the proteins or protein fragments identified according to the invention which can comprise as a further component autofluorescent markers like, for example, GFP or cytostatic drugs like, for example, cholera toxin.

Pharmaceutically acceptable carriers and/or auxiliary substances comprises substances which stabilize the binding substance and the protein of protein fragments, respectively, or variants thereof, which increase the pharmaceutical tolerance or which are required by the respective form or application like for example tablet, band aid or infusion solution as, for example, preservative, buffer, salt or protease inhibitors.

A further aspect of the present, invention is a kit for producing a mixture of nucleic acids according to claim 10 comprising:
a) at least one first nucleic acid, comprising at least one restriction site 5' and/or 3' of a nucleic acid coding for a first fusion protein comprising:
   i) an interaction domain and
   ii) a protein translocation sequence which effects that the first fusion protein upon expression in a bacterium is translocated through the cytoplasmic membrane in an essentially folded state.

This kit allows the insertion of a chosen nucleic acid sequence 5' or 3' of the nucleic acid which codes for the interaction domain and the protein translocation sequence with the result that the resulting nucleic acid codes for a fusion protein which comprises at its C-terminus and/or at its N-terminus a protein or protein fragment encoded by the respectively introduced nucleic acid sequence. Preferably, the introduced DNA is a cDNA library, wherein this is particularly preferred if it and has been introduced into the nucleic acid by using the 3'-restriction site. In a preferred embodiment the kit comprises the leucine zipper of the cFos protein and in a further preferred embodiment the Tat dependent protein translocation sequence TorA.

In a further embodiment of the kit the kit according to the present invention further comprises at least a second nucleic acid comprising at least one restriction site 5' and/or 3' of a nucleic acid coding for a second fusion protein comprising:
   i) an interaction domain and
   ii) a protein translocation sequence which effects that the second fusion protein upon expression in a bacterium is translocated through the cycloplasmic membrane in an essentially unfolded state, wherein the interaction domain of the first fusion protein can bind to those of the second fusion protein.

This nucleic acid allows insertion 5' or 3' of the nucleic acid encoding for the interaction domain and the protein translocation sequence so that in result the resulting nucleic acid codes for a fusion protein which comprises at is N- or C-terminus a protein or protein fragment coded for by the inserted nucleic acid. For example nucleic acids coding for a phage coat protein can be inserted into a nucleic acid wherein those are preferably inserted at the 3' restriction site.

It has been shown that if nucleic acids coding for phage coat proteins are introduced into the second nucleic acid that the resulting fusion protein upon strong expression of, for example, the gIIIp-fusion protein lead to high toxicity in *E. coli* cells. For this reason an amber codon is inserted in classical phase display systems 5' of the gIII-protein. In suppressor strains (e.g. CL-1 Blue) the expression of the gIIIp-fusion protein is thereby reduced by 90%. Furthermore the amber codon (which is read in non-suppressor strains as STOP codon) enables the easy soluble expression of the protein which was previously fused with a phage protein and presented on the phage by introducing the phagimid into a non suppressor strain (e.g. BL21) and expressing it therein. Accordingly, the first and/or the second nucleic acid comprises in a preferred embodiment either 5' or 3' an amber codon. Preferably, the amber codon is positioned in the first nucleic acid 5' and in the second nucleic acid 3'. Thereby it is possible that only the protein or protein fragment, which has been inserted into the first nucleic acid 5' is expressed in a suitable host and at the same time that the toxic effect of the gIIIp which is inserted into the second nucleic acid 3' is prevented.

In a further preferred embodiment of the kit according to the invention the interactive domain of the second fusion protein is a leucin zipper domain of the cJun protein. In a further preferred embodiment the nucleic acid comprises a nucleic acid which codes for a Sec-dependent protein translocation sequence in particular the PelB leader peptide.

A further aspect of the present invention is the use of a cell for the production of a protein mix according to the invention as well as the use of a protein mix according to the invention, a vector according to the invention or a cell according to the invention for the preparation of a library according to the invention.

A preferred area of using the protein mixes of the invention, the phages of the invention, the cells of the invention in particular the libraries of the invention comprising the above referenced mixtures of proteins, phages and cells as well as of using the kits of the present invention is the presentation of proteins on filamentous phages. A particular focus thereby is on proteins which due to the incompatibility with the Sec transport pathway cannot be presented using the classical phage display technology. As a result of this presentation and selection of cDNA expression libraries and the presentation and selection of DNA libraries for directed evolution of proteins also called "protein engineering" are particularly preferred areas of application.

A further preferred use is the production of protein conjugates. Thereby the use is particularly preferred when the protein or protein fragment of the first fusion protein and the protein or protein fragment of the second fusion protein respectively have different requirements for the cellular environment required for correct folding. Thereby the present invention allows the direct fusion of antibodies with marker proteins which would not be correctly folded upon production in bacteria and transport through the Sec-dependent transport pathway and which could, therefore, not be used in standard procedures as marker proteins for marking antibodies. Marker protein antibody fusions the functional expression of which is only enabled by the present invention comprise, for example, fusions of autofluorescent proteins like GFP and immune globulin heavy chains, immune globulin light chains or "single chain antibodies".

The following illustrations and examples are merely provided as an illustration of the invention and not as a limitation to the specific embodiments indicated in the examples. All references comprised in the text are hereby incorporated by reference in their entirety.

FIGURES

FIG. 1 Consensus sequence of Tat-dependent, Sec-dependent, SRP-dependent or YidY-dependent signal sequences wherein X is a random amino acid and # is a hydrophobic amino acid.

FIG. 2 Tat-dependent TorA-signal peptide, wherein X is a random amino acid and # is a hydrophobic amino acid.

FIG. 3 Underlying principle of the TLF-system, wherein CT represents the pIII domain, pelB the Sec signal sequence, TSS the Tat signal sequence and POI the presented protein.

Figure 4:
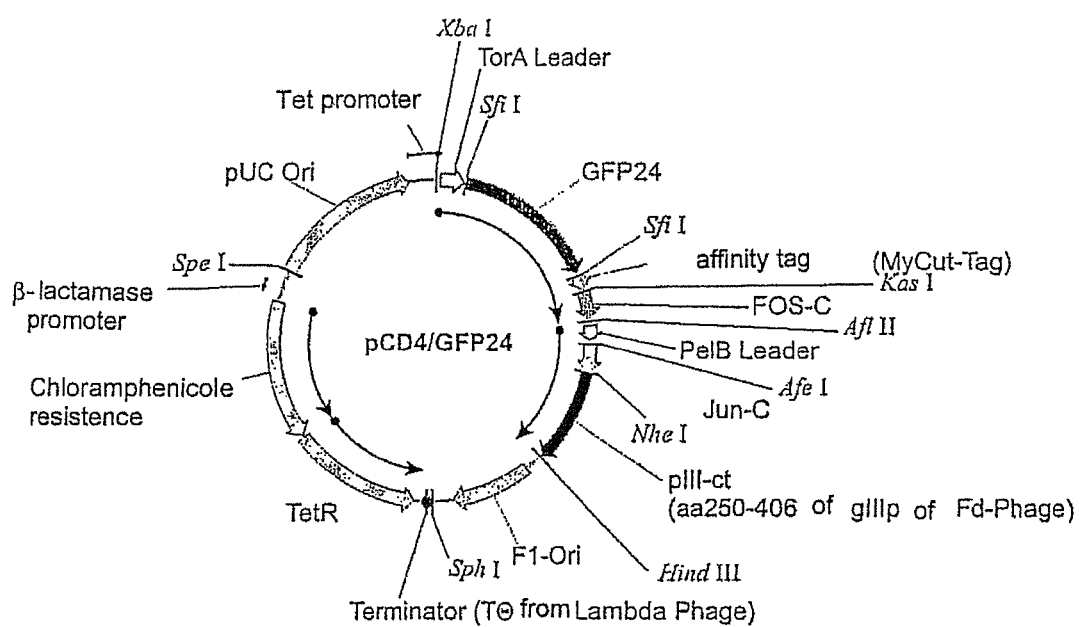

FIG. 4 Restriction map of the plasmid pCD4/GFP24 the nucleic acid sequence of which is depicted in the appendix as SEQ ID NO: 1.

Figure 5:
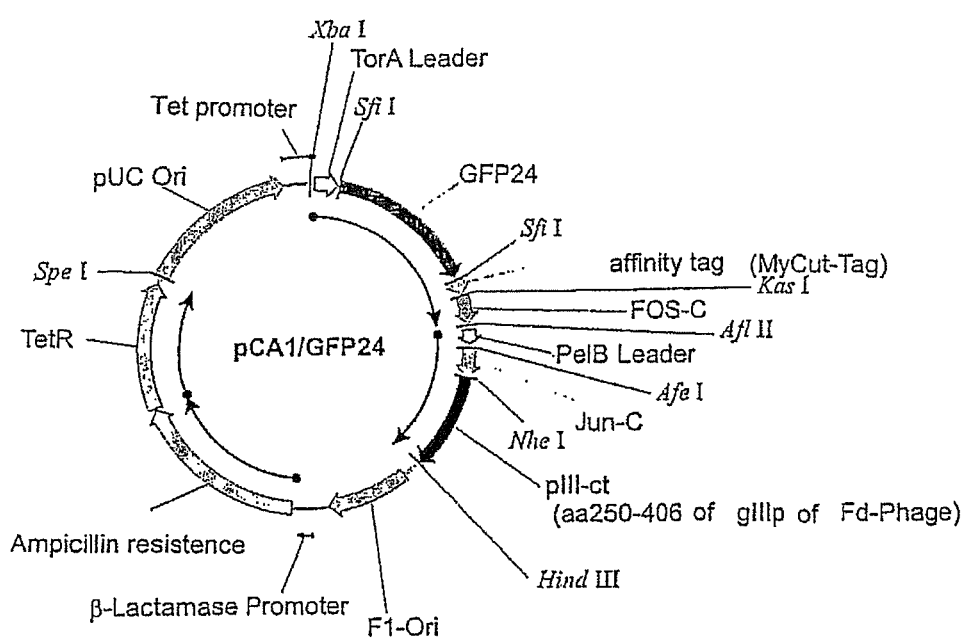

FIG. 5 Restriction map of the plasmid pCA1/GFP24 the nucleic acid sequence of which is depicted in SEQ ID NO: 2.

Figure 6:
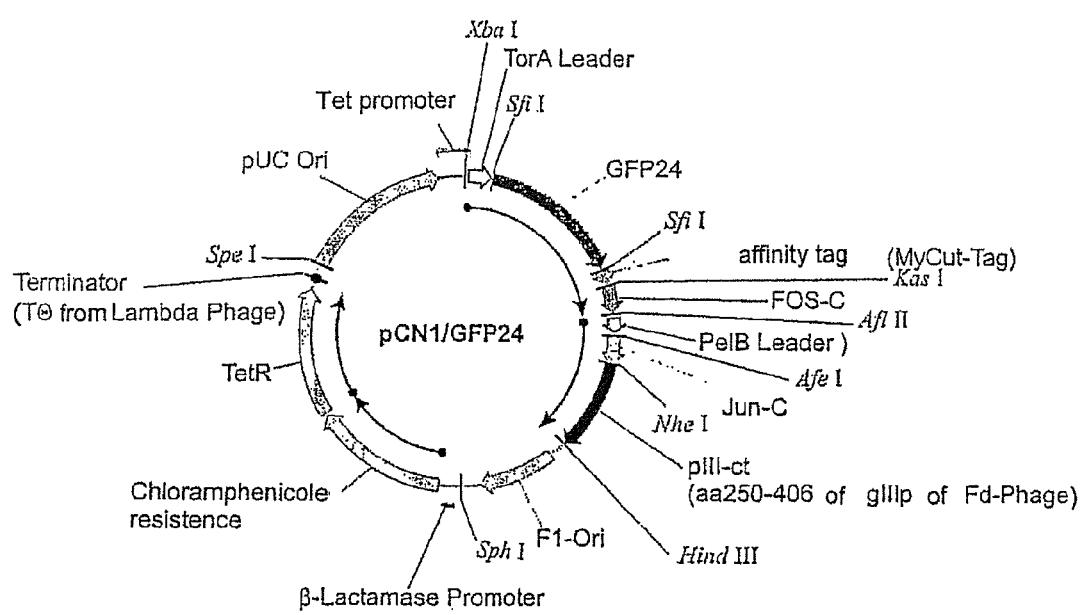

FIG. 6 Restriction map of the plasmid pCN1/GFP24 the nucleic acid of which is depicted in SEQ ID NO: 3.

Figure 7:
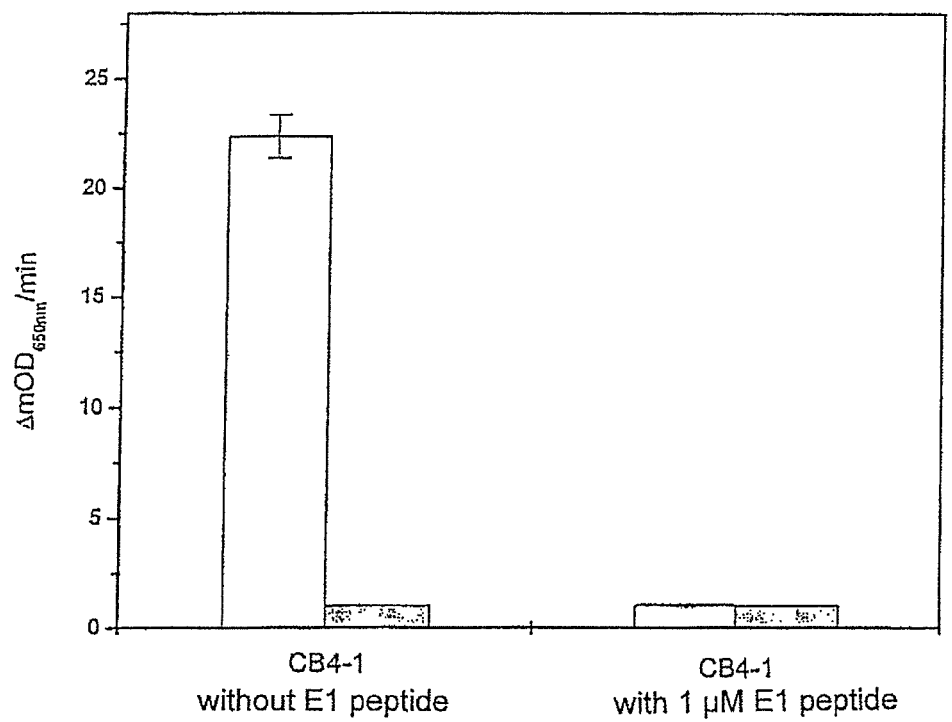

FIG. 7 Competitive phage ELISA wherein white bars represent the results with GFP24 presenting phages. GFP24 phages were made with the help of XL-1 blue cells carrying the pCD4/GFP24 plasmid. Grey bars represent the results which were obtained with β-lactamase carrying phages. The β-lactamase presenting phages were made in XL-1 blue cells which carried the plasmid pCD4/BLA.

Figure 8:
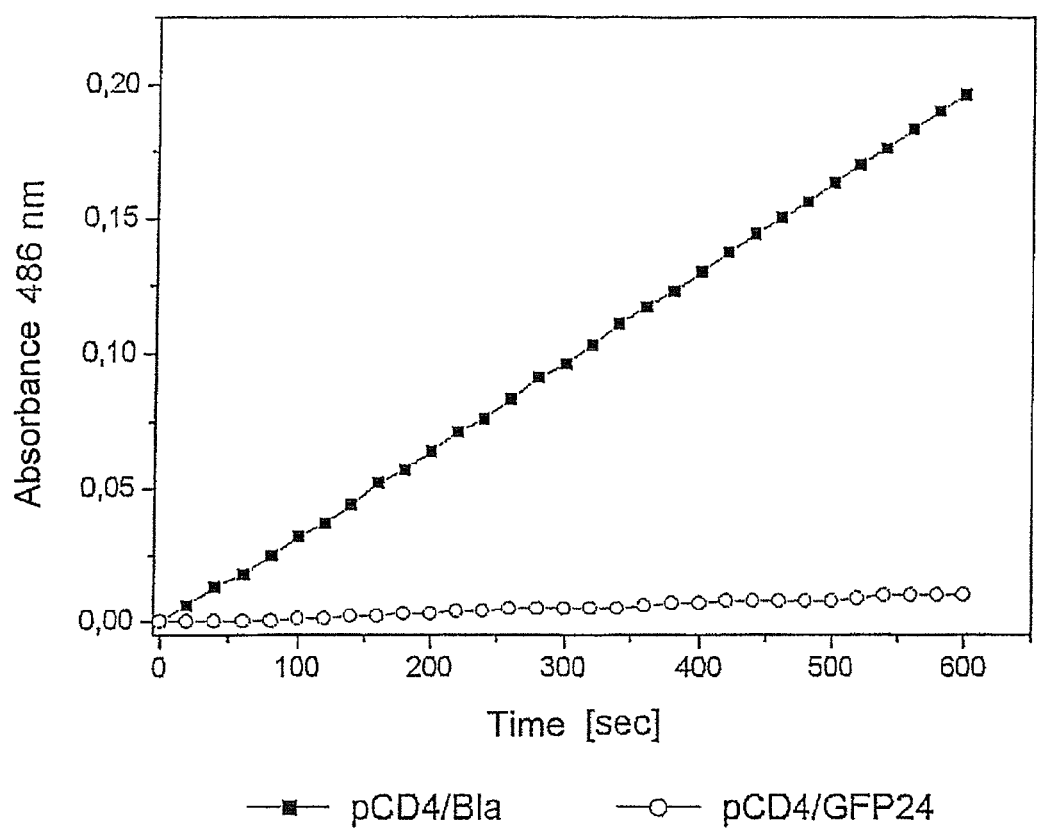

FIG. 8 Enzymatic assay of the presentation of β-lactamase on bacteriophages wherein white circles represent the results with GFP24 carrying phages. The GFP24 phages were made with the help of XL-1 blue cells which carry the pCD4/GFP24 plasmid. Black squares represent the results which were obtained with phages carrying the β-lactamase. β-lactamase presenting phages were produced with XL-1 blue cells carrying the pCD4/BLA plasmid. The absorption at 486 nm in relation to the time is shown.

EXAMPLES

Example 1

Vectors Used pCD4/GFP24 is a cystein display phagimid which is based on the pGP-vector (Paschke M., et al.: (2001) Biotechniques 30: 720-725).

pCAI/GFP24 is a cystein display phagimid which is based on pGF-F100. It can be used for the $tet^{o-p}$ controlled expression of proteins as fusion of cFos leucin zipper. The translocation of the cFos-fusion protein into the periplasmatic space is mediated by the TorA leader peptide sequence (Tat-dependent translocation pathway). The $tet^{o-p}$ controlled transcript comprises a second cistron which expresses the c-jun::G3Ps fusion protein. The c-Jun::G3Ps is directed into the periplasmatic space through the Sec-dependent translocation pathway. Covalent complexes between the cFos-fusion protein and the cJun::G3PS fusion protein are formed in the periplasmatic space due to the dimerization of cJun and cFos and subsequent formation of cystein bonds between the proteins. The phagimid comprises a GFP24 cassette flanked by SfiI restriction sites at positions 148 and 910 and is positioned between the TorA leader peptide and cFos. This cassette has to be replaced by a protein to be presented.

pCAI/GFP24 is a cystein display phagimid derived from pCD4, which is based on a pGP vector. pDC4/GFP24 is a cystein display phagimid that is based on the pGP vector (Paschke M., et al.: (2001) Biotechniques 30: 720-725). It can be used for the $tet^{o-p}$ controlled expression of proteins as fusion with the cFos leucin zipper. The translocation of the cFos fusion protein to the periplasmatic space is mediated by the TorA leader peptide (Tat transport pathway). The $tet^{o-p}$ controlled transcript comprises a second cistron, which expresses the c-jun::G3Pss fusion protein (G3Pss comprises amino acid 252 to 406 of the mature gIII proteins of the fd phage). The c-jun::G3Pss is directed towards the periplasmatic space through a Sec-dependent transport pathway (pelB leader peptide). Covalent complexes of cFos fusion protein and c-jun::G3Pss are formed due to the dimerization between cJun and cFos in the periplasmatic space and the subsequent formation of cystein bonds between the proteins (Crameri, R. and Suter M. (1993), supra). The phage display of the proteins, which are fused with cFos can be achieved by so-called helper phage rescue. In contrast to pGP the phagimid pCD4-GFP24 converts chloramphenicol resistance. The resistance gene (CAT) and the tet-repressor (TetR) are under the control of β-lactamase promoter as a bicistronic cassette. The transcript is terminated in a λ-phage terminator. The Tat-TetR cassette is in a reversed position towards the cFos and the cJun fusion cassette. A GFP24 cassette flanked at the positions 148 and 910 by Sfi1 restrictions sites is positioned between the TorA leader peptide and cFos. This cassette is replaced by the protein to be presented.

pCD4/Bla is a cystein display phagimid derived from pDC4/GFP24 wherein through restriction digest with Sfi1 the GFP24 fragment has been replaced by the sequence of the mature TEM1 β-lactamase. The inserted lactamase cloning cassette with 5' and 3' terminal SfiI restrictions sites is depicted in SEQ ID NO:4.

Example 2

Production of Bacterio Phages

XL1 blue cells transformed with the respective phagimid were cultivated in 2 TY selection media at 30° C. to an $OD_{600\ nm}$ of 0.5 and then mixed with the helper phage VCSM13 at a Moi=10-20. The infected culture was cultivated for 30 minutes at 37° C. and subsequently mixed with kanamizin at a final concentration of 60 µg/ml. The culture was cultivated at 25° C. for 10 minutes. The cells were harvested by centrifugation (4000×g, 4° C., 5 minutes) and subsequently resuspended in T2Y selection medium comprising 60 µg/ml kanamizin and 0.5 µg/ml tetracycline. The culture was cultivated for 5 hours at 25° C. Subsequently, phage preparation from the cell culture supernatant followed as follows: 40-50 ml cells and cell debris each were separated by centrifugation from phage comprising cell culture supernatant (4° C., 10,000 rpm in an A8-24 rotor for 15 minutes). The supernatant was filtered through a 0.45 µm filter and was mixed with ¼ volume PEG-NaCl solution (20% w/v PEG 8000, 50% w/v NaCl) and incubated on ice over night or at least for 5 hours. The mixture was then centrifuged at 4° C. for 15 minutes with 15,000 rpm in an A8.24 rotor. The pellet was resuspended in 2.5 ml ice cold PBS and distributed into 2 ml plastic tubes. Then the supernatant was mixed with ¼ A volumes PEG-NaCl solution and incubated on ice for at least one further hour. Then the supernatant was centrifuged at 4° C. and 14,000 rpm for 15 minutes. The phage pellet was dissolved in 0.5-1 ml PBS. If necessary the phage solution was filtered through a 0.45 µm filter and then stored at 4° C. For long term storage the phage solution was mixed with 1 volume glycerine and stored at −70° C.

Phage titre was determined using standard methods employing serial dilutions. The titre usually was in the range of $10^{12}$ and $10^{13}$ cfu/ml.

Example 3

Presentation of Functional GFP24 on Phage

GFP24 is a variant of a green fluorescent protein with a circular permutation which further comprises an epitope of the P24 protein of HIV (Mine, W. E. et al. (1993) Mol. Immunol. 30:1213-21). GFP24 is bound with high affinity by the anti-P24 antibody CB4-1 (Dr. Scholz, Institute for Biochemistry (Universitätsklinikum Charité)). Similar to GFP GFP24 cannot be exported through the Sec-transport pathway. A functional GFP24 protein should resulting from expression of the above described pCD4/GFP24 plasmid should, thus, only lead to the presentation of a functional GFP24, if this part of the protein is not transported into the periplasma by a Sec-dependent transport pathway but rather by a Tat-dependent transport pathway. To detect GFP24 on filamentous phage a phage-ELISA was carried out as follows: microtitre plates were coated with 10 µm/ml anti-P24 antibody C4-1, washed three times with PBS/Tween 0.1% and incubated for 1 to 2 hours per well with Genosys blocking reagent (Sigma-Genosys Ltd., Cambridge, UK) at room temperature under shaking. Subsequently the microtitre plate was washed three times with PBS/Tween 20 0.1%. Then 50 µl of GFP24 presenting phage with or without P24 peptide was placed in the well of the micro titre plate and then the presence of phage in the microtitre plate was detected with a horseradish peroxidase coupled anti-phage antibody (Seramun Diagnostica GmbH, Dolgenbrodt, Germany). Signal intensity represented the phage bound to CB4-1. pCD4/GFP24 phage was completely replaced from CB4-1 through the P24 peptide while β-lactamase presenting phages (pCD4/BLA) which were used as a control did not bind to CB4-1. On top of that no unspecific binding to other antibodies or to the blocking reagents could be detected (see FIG. 7).

Example 4

Presentation of TEM1-β-Lactamase on Filamentous Phages

TEM-1-β-lactamase is a periplasmatic protein which can confer resistance to ampicillin by hydrolysis of the lactam ring of the antibiotic ampicillin. TEM-1-β-lactamase is usually exported into the periplasma through a Sec-dependent transport pathway. To show that TEM-1-β-lactamase can also be exported through a Tat-dependent transport pathway the Sec-signal sequence was removed and replaced by the TorA-sequence. The successful presentation of TEM-1-β-lactamase was determined with an enzyme assay described in the following, the results of which are depicted in FIG. 8. 800 µl PBS pH 7.4 were mixed with 100 µl nitrocefin stock solution (500 µg/ml) and adapted to 25° C. 100 µl phage solution were added. The change of extinction at 486 nm was determined photometrically over 10 min. The change of absorption at 486 nm corresponds to the β-lactamase activity of the phage. While pCD4/GFP24 phages exhibited no β-lactamase activity it was possible to detect a strong β-lactamase activity for pCD4/BLA.

The nitrocefin stock solution was prepared as follows: 1 mg nitrocefin was dissolved in 100 µl DMSO. The solution was then mixed with 1.9 ml PBS. The solution was stored at −20° C. for a maximum of 2 weeks.

The invention claimed is:

1. A method of identifying proteins or protein fragments which bind to a test substance comprising the following steps:
    (a) contacting at least one test substance with a library of protein mixtures,
        wherein said library comprises at least two protein mixtures,
        wherein each protein mixture in the library comprises at least a first fusion protein and at least a second fusion protein,
        wherein said first fusion protein comprises
            (i) a phage coat protein,
            (ii) a leucine zipper domain as interaction domain, and
            (iii) a Sec-dependent protein translocation sequence,
        wherein said second fusion protein comprises
            (iv) a protein or protein fragment,
            (v) a leucine zipper domain as interaction domain, and
            (vi) a Tat dependent protein translocation sequence,
        wherein the interaction domain of the first fusion protein is covalently bound to the interaction domain of the second fusion protein via cysteine residues,
        wherein the interaction domain of the first fusion protein is the leucine zipper domain of the cJun protein and the interaction domain of the second fusion protein is the leucine zipper domain of the cFos protein,
        wherein the proteins or protein fragments of the respective second fusion proteins are different from each other; and
    (b) measuring of the respective binding of the test substance to the different protein mixtures of the library.

2. The method according to claim 1, wherein the protein or protein fragment of the second fusion protein is a protein that is encoded by a cDNA derived from a cDNA library, a synthetic protein, an enzyme, a cofactor-dependent protein, or an autofluorescent protein.

3. The method according to claim 1, wherein the test substance is a protein or protein fragment.

4. The method according to claim 1, wherein contacting at least one test substance with a library of protein mixtures means any possibility of interaction between the test substance and the protein mixtures, wherein said at least one test substance and said protein mixtures can be independently of each other in liquid phase or attached to a solid phase.

5. The method according to claim 4, wherein the at least one test substance is immobilized on a solid surface and is contacted with the protein mixtures.

6. The method according to claim 5, wherein the measuring of the binding of the test substance to the protein mixtures is carried out by measuring a fluorescent or radioactive marker connected to the protein mixture, by detecting a change of electrochemical properties, or by potentiometric methods.

7. The method according to claim 1, wherein the phage coat protein is selected from the M13 phage coat proteins pIII, pVI, pVII, pVIII and pIX.

8. The method according to claim 1 comprising the further steps:
    (c) selecting at least one protein mixture on the basis of the measured binding, and
    (d) generating a second library wherein the library is generated by modification of the protein or protein fragment comprised in the selected protein mixture.

9. The method according to claim 1 comprising the further steps:
    (c) selecting at least one protein mixture on the basis of the measured binding,
    (d) producing a second library, wherein the library is created through the modification of the protein or protein fragment comprised in the selected protein mixture,
    (e) contacting at least one test substance with the second library,
    (f) measuring of the respective binding of the test substance to the different protein mixtures of the second library, and
    (g) if the case may be, repeating of steps (c) to (f) until a protein mixture is selected which exhibits the desired binding.

10. The method according to claim 8, wherein the modification of the protein or protein fragment comprised in the selected protein mixture in step (d) is obtained by random mutagenesis or by targeted substitution of single nucleic acid codons of a nucleic acid coding for said protein or protein fragment.

11. The method according to claim 9, wherein the modification of the protein or protein fragment comprised in the selected protein mixture in step (d) is obtained by random mutagenesis or by targeted substitution of single nucleic acid codons of a nucleic acid coding for said protein or protein fragment.

* * * * *

SEQUENCE LISTING

```
<160> NUMBER OF SEQ ID NOS: 11

<210> SEQ ID NO 1
<211> LENGTH: 4765
<212> TYPE: DNA
<213> ORGANISM: Artificial Sequence
<220> FEATURE:
<223> OTHER INFORMATION: synthetic expression and cloning vector derived
      from E. coli

<400> SEQUENCE: 1
```

```
ctagataaga aggaagaaaa ataatgaaca ataacgatct ctttcaggca tcacgtcggc      60
gttttctggc acaactcggc ggcttaaccg tcgccgggat gctggggccg tcattgttaa     120
cgccgcgacg tgcgactgcg gcccagccgg ccatggcggg atccgttcaa ctagcagacc     180
attatcaaca aaatactcca attggcgatg gccctgtcct tttaccagac aaccattacc     240
tgtcgacaca atctgccctt tcgaaagatc caacgaaaa gcgtgaccac atggtccttc      300
ttgagtttgt aactgctgct gggatttccg gtggtggtgg tgctaccccg caggacctga     360
acaccatgct gggtggtggt ggtagtaaag gagaagaact tttcactgga gttgtcccaa     420
ttcttgttga attagatggt gatgttaatg ggcacaaatt ttctgtcagt ggagagggtg     480
aaggtgatgc aacatacgga aaacttaccc ttaaatttat ttgcactact ggaaaactac     540
ctgttccatg gccaacactt gtcactactt tctcttatgg tgttcaatgc ttttcccgtt     600
atccggatca tatgaaacgg catgactttt tcaagagtgc catgcccgaa ggttatgtac     660
aggaacgcac tatatctttc aaagatgacg ggaactacaa gacgcgtgct gaagtcaagt     720
ttgaaggtga taccctggtt aatcgtatcg agttaaaagg tattgatttt aagaagatg      780 gaaacattct cggacacaaa ctcgagtaca actataactc acacaatgta tacatcacgg     840
cagacaaaca aaagaatgga atcaaagcta acttcaaaat tcgccacaac attgaagatt     900
cggcctcggg ggccgcagaa caaaaactca tctcagaaga gatctgtat ttccagggcg      960 atgcttgcgg tggcaccgac accctgcaag ctgaaaccga ccagctggaa gacgagaaat    1020
ccgctctgca gactgaaatc gctaacctgc tgaaagagaa agagaaactg gaattcattc    1080
tggctgctca cggcggttgt gggctaggct aataacttaa gccaaggagg aaaataaaat    1140
gaaataccta ttgcctacgg cagccgctgg attgttatta ctcgcggcac agccggccat    1200
ggcaagcatc tgcggtggcc gtatcgctcg tctggaagaa aaagttaaaa ccctgaaagc    1260
tcagaactcc gaactggctt ccaccgctaa catgctgcgt gaacaggttg ctcagctgaa    1320
gcagaaagtt atgaaccacg gcggttgtgg tggcggttcc ctagcgggct ccggttccgg    1380 tgatttgat tatgaaaaaa tggcaaacgc taataagggg gctatgaccg aaaatgccga     1440
tgaaaacgcg ctacagtctg acgctaaagg caaacttgat tctgtcgcta ctgattacgg    1500
tgctgctatc gatggtttca ttggtgacgt ttccggcctt gctaatggta atggtgctac    1560
tggtgatttt gctggctcta attcccaaat ggctcaagtc ggtgacggtg ataattcacc    1620
tttaatgaat aatttccgtc aatatttacc ttctttgcct cagtcggttg aatgtcgccc    1680 ttatgtctttt ggcgctggta aaccatatga attttctatt gattgtgaca aaataaactt    1740
attccgtggt gtctttgcgt ttcttttata tgttgccacc tttatgtatg tattttcgac    1800
gtttgctaac atactgcgta ataaggagtc ttaataagct tgacctgtga agtgaaaaat    1860
ggcgcacatt gtgcgacatt ttttttgtct gccgtttacc gctactgcgt cacggatctc    1920
cacgcgccct gtagcggcgc attaagcgcg gcgggtgtgg tggttacgcg cagcgtgacc    1980
gctacacttg ccagcgccct agcgcccgct cctttcgctt tcttcccttc ctttctcgcc    2040
acgttcgccg gctttccccg tcaagctcta aatcggggc tccctttagg gttccgattt    2100
agtgctttac ggcacctcga ccccaaaaaa cttgattagg gtgatggttc acgtagtggg    2160 ccatcgcccct gatagacggt ttttcgccct ttgacgttgg agtccacgtt ctttaatagt    2220
ggactcttgt tccaaactgg aacaacactc aaccctatct cggtctattc ttttgattta    2280
taagggattt tgccgatttc ggcctattgg ttaaaaaatg agctgattta acaaaaattt    2340
aacgcgcatg ctaacaaaat attaaaaaac gcccggcggc aaccgagcgt taatagtgaa    2400
```

```
gttaccatca cggaaaaagg ttatgctgct tttaagaccc actttcacat ttaagttgtt    2460
tttctaatcc gcatatgatc aattcaaggc cgaataagaa ggctggctct gcaccttggt    2520
gatcaaataa ttcgatagct tgtcgtaata atggcggcat actatcagta gtaggtgttt    2580
cccttttctt tttagcgact tgatgctctt gatcttccaa tacgcaacct aaagtaaaat    2640
gccccactgc gctgagtgca tataatgcat tctctagtga aaaaccttgt tggcataaaa    2700
aggctaattg attttcgaga gtttcatact gttttttctgt aggccgtgta cctaaatgta    2760
cttttgctcc atcgcgatga cttagtaaag cacatctaaa acttttagcg ttattacgta    2820
aaaaatcttg ccagctttcc ccttctaaag ggcaaaagtg agtatggtgc ctatctaaca    2880
tctcaatggc taaggcgtcg agcaaagccc gcttattttt tacatgccaa tacaatgtag    2940
gctgctctac acctagcttc tgggcgagtt tacgggttgt taaaccttcg attccgacct    3000
cattaagcag ctctaatgcg ctgttaatca ctttactttt atctaaacga gacatcatta    3060
attcctatta cgccccgccc tgccactcat cgcagtactg ttgtaattca ttaagcattc    3120
tgccgacatg gaagccatca caaacggcat gatgaacctg aatcgccagc ggcatcagca    3180
ccttgtcgcc ttgcgtataa tatttgccca tagtgaaaac gggggcgaag aagttgtcca    3240
tattggccac gtttaaatca aaactggtga aactcaccca gggattggct gagacgaaaa    3300
acatattctc aataaaccct ttagggaaat aggccaggtt ttcaccgtaa cacgccacat    3360
cttgcgaata tatgtgtaga aactgccgga aatcgtcgtg gtattcactc cagagcgatg    3420
aaaacgtttc agtttgctca tggaaaacgg tgtaacaagg gtgaacacta tcccatatca    3480
ccagctcacc gtctttcatt gccatacgga attccggatg agcattcatc aggcgggcaa    3540
gaatgtgaat aaaggccgga taaaacttgt gcttattttt ctttacggtc tttaaaaagg    3600
ccgtaatatc cagctgaacg gtctggttat aggtacattg agcaactgac tgaaatgcct    3660
caaaatgttc tttacgatgc cattgggata tatcaacggt ggtatatcca gtgatttttt    3720
tctccatact cttccttttt caatattatt gaagcattta tcagggttat tgtctcatga    3780
gcggatacat atttgaatgt atttagaaaa ataaacaaat aggggttccg cgcacatttc    3840
cccgaaaagt gccacctgaa attgtaagcg ttactagttt aaaaggatct aggtgaagat    3900
cctttttgat aatctcatga ccaaaatccc ttaacgtgag ttttcgttcc actgagcgtc    3960
agaccccgta gaaaagatca aaggatcttc ttgagatcct ttttttctgc gcgtaatctg    4020
ctgcttgcaa acaaaaaaac caccgctacc agcggtggtt tgtttgccgg atcaagagct    4080
accaactctt tttccgaagg taactggctt cagcagagcg cagataccaa atactgtcct    4140
tctagtgtag ccgtagttag gccaccactt caagaactct gtagcaccgc ctacatacct    4200
cgctctgcta atcctgttac cagtggctgc tgccagtggc gataagtcgt gtcttaccgg    4260
gttggactca agacgatagt taccggataa ggcgcagcgg tcgggctgaa cggggggttc    4320
gtgcacacag cccagcttgg agcgaacgac ctacaccgaa ctgagatacc tacagcgtga    4380
gctatgagaa agcgccacgc ttcccgaagg gagaaaggcg gacaggtatc cggtaagcgg    4440
cagggtcgga acaggagagc gcacgaggga gcttccaggg ggaaacgcct ggtatcttta    4500
tagtcctgtc gggtttcgcc acctctgact tgagcgtcga ttttttgtgat gctcgtcagg    4560 ggggcggagc ctatgaaaaa acgccagcaa cgcggccttt ttacggttcc tggccttttg    4620
ctggcctttt gctcacatga cccgacacca tcgaatggcc agatgattaa ttcctaattt    4680
ttgttgacac tctatcattg atagagttat tttaccactc cctatcagtg atagagaaaa    4740
gtgaaatgaa tagttcgaca aaaat                                         4765
```

<210> SEQ ID NO 2
<211> LENGTH: 4971
<212> TYPE: DNA
<213> ORGANISM: Artificial Sequence
<220> FEATURE:
<223> OTHER INFORMATION: synthetic expression and cloning vector derived
      from E. coli

<400> SEQUENCE: 2

| | | | | | |
|---|---|---|---|---|---|
| ctagataaga | aggaagaaaa | ataatgaaca | ataacgatct | ctttcaggca | tcacgtcggc | 60 |
| gttttctggc | acaactcggc | ggcttaaccg | tcgccgggat | gctggggccg | tcattgttaa | 120 |
| cgccgcgacg | tgcgactgcg | gcccagccgg | ccatggcggg | atccgttcaa | ctagcagacc | 180 |
| attatcaaca | aaatactcca | attggcgatg | gccctgtcct | tttaccagac | aaccattacc | 240 |
| tgtcgacaca | atctgccctt | tcgaaagatc | ccaacgaaaa | gcgtgaccac | atggtccttc | 300 |
| ttgagtttgt | aactgctgct | gggatttccg | gtggtggtgg | tgctaccccg | caggacctga | 360 |
| acaccatgct | gggtggtggt | ggtagtaaag | gagaagaact | tttcactgga | gttgtcccaa | 420 |
| ttcttgttga | attagatggt | gatgttaatg | ggcacaaatt | ttctgtcagt | ggagagggtg | 480 |
| aaggtgatgc | aacatacgga | aaacttaccc | ttaaatttat | ttgcactact | ggaaaactac | 540 |
| ctgttccatg | gccaacactt | gtcactactt | tctcttatgg | tgttcaatgc | ttttcccgtt | 600 |
| atccggatca | tatgaaacgg | catgactttt | tcaagagtgc | catgcccgaa | ggttatgtac | 660 |
| aggaacgcac | tatatctttc | aaagatgacg | ggaactacaa | gacgcgtgct | gaagtcaagt | 720 |
| ttgaaggtga | taccttgtt | aatcgtatcg | agttaaaagg | tattgatttt | aaagaagatg | 780 |
| gaaacattct | cggacacaaa | ctcgagtaca | actataactc | acacaatgta | tacatcacgg | 840 |
| cagacaaaca | aaagaatgga | atcaaagcta | acttcaaaat | tcgccacaac | attgaagatt | 900 |
| cggcctcggg | ggccgcagaa | caaaaactca | tctcagaaga | gaatctgtat | ttccagggcg | 960 |
| ggcccaaacc | ttccaccccg | cctggttctt | caggcgcctg | cggtggcctg | accgacaccc | 1020 |
| tgcaagctga | aaccgaccag | ctggaagacg | agaaatccgc | tctgcagact | gaaatcgcta | 1080 |
| acctgctgaa | agagaaagag | aaactggaat | tcattctggc | tgctcacggc | ggttgttaat | 1140 |
| aacttaagcc | aaggaggaaa | ataaaatgaa | ataccattg | cctacggcag | ccgctggatt | 1200 |
| gttattactc | gctgcccaac | cagcgatggc | cgcacaggtt | aaactgctcg | agagcgcttg | 1260 |
| cggtggccgt | atcgctcgtc | tggaagaaaa | agttaaaacc | ctgaaagctc | agaactccga | 1320 |
| actggcttcc | accgctaaca | tgctgcgtga | acaggttgct | cagctgaagc | agaaagttat | 1380 |
| gaaccacggc | ggttgtgcta | gcggtggcgg | ctccggttcc | ggtgattttg | attatgaaaa | 1440 |
| aatggcaaac | gctaataagg | gggctatgac | cgaaaatgcc | gatgaaaacg | cgctacagtc | 1500 |
| tgacgctaaa | ggcaaacttg | attctgtcgc | tactgattac | ggtgctgcta | tcgatggttt | 1560 |
| cattggtgac | gttccggcc | ttgctaatgg | taatggtgct | actggtgatt | ttgctggctc | 1620 |
| taattcccaa | atggctcaag | tcggtgacgg | tgataattca | cctttaatga | ataatttccg | 1680 |
| tcaatattta | ccttctttgc | ctcagtcggt | tgaatgtcgc | ccttatgtct | ttggcgctgg | 1740 |
| taaaccatat | gaattttcta | ttgattgtga | caaaataaac | ttattccgtg | gtgtctttgc | 1800 |
| gtttctttta | tatgttgcca | cctttatgta | tgtattttcg | acgtttgcta | acatactgcg | 1860 |
| taataaggag | tcttaataag | cttgacctgt | gaagtgaaaa | atggcgcaca | ttgtgcgaca | 1920 |
| ttttttttgt | ctgccgttta | ccgctactgc | gtcacggatc | tccacgcgcc | ctgtagcggc | 1980 |
| gcattaagcg | cggcgggtgt | ggtggttacg | cgcagcgtga | ccgctacact | tgccagcgcc | 2040 |

```
ctagcgcccg ctcctttcgc tttcttccct tcctttctcg ccacgttcgc cggctttccc    2100
cgtcaagctc taaatcgggg gctcccttta gggttccgat ttagtgcttt acggcacctc    2160
gaccccaaaa aacttgatta gggtgatggt tcacgtagtg ggccatcgcc ctgatagacg    2220 gttttcgcc ctttgacgtt ggagtccacg ttctttaata gtggactctt gttccaaact    2280
ggaacaacac tcaaccctat ctcggtctat tcttttgatt tataagggat tttgccgatt    2340
tcggcctatt ggtaaaaaa tgagctgatt taacaaaaat ttaacgcgaa ttttaacaaa    2400
atattaacgc ttacaatttc aggtggcact tttcggggaa atgtgcgcgg aaccctatt    2460 tgtttatttt tctaaataca ttcaaatatg tatccgctca tgagacaata accctgataa    2520
atgcttcaat aatattgaaa aggaagagt atgagtattc aacatttccg tgtcgccctt    2580
attccctttt ttgcggcatt ttgccttcct gttttgctc acccagaaac gctggtgaaa    2640
gtaaaagatg ctgaagatca gttgggtgca cgagtgggtt acatcgaact ggatctcaac    2700
agcggtaaga tccttgagag ttttcgcccc gaagaacgtt ttccaatgat gagcactttt    2760
aaagttctgc tatgtggcgc ggtattatcc cgtattgacg ccgggcaaga gcaactcggt    2820
cgccgcatac actattctca gaatgacttg gttgagtact caccagtcac agaaaagcat    2880
cttacggatg gcatgacagt aagagaatta tgcagtgctg ccataaccat gagtgataac    2940
actgcggcca acttacttct gacaacgatc ggaggaccga aggagctaac cgcttttttg    3000
cacaacatgg gggatcatgt aactcgcctt gatcgttggg aaccggagct gaatgaagcc    3060
ataccaaacg acgagcgtga caccacgatg cctgtagcaa tggcaacaac gttgcgcaaa    3120
ctattaactg gcgaactact tactctagct tcccggcaac aattgataga ctggatggag    3180
gcggataaag ttgcaggacc acttctgcgc tcggcccttc cggctggctg gtttattgct    3240
gataaatctg gagccggtga gcgtggctct cgcggtatca ttgcagcact ggggccagat    3300
ggtaagccct cccgtatcgt agttatctac acgacgggga gtcaggcaac tatggatgaa    3360
cgaaatagac agatcgctga gataggtgcc tcactgatta gcattggta ggaattaatg    3420 atgtctcgtt tagataaaag taaagtgatt aacagcgcat tagagctgct taatgaggtc    3480
ggaatcgaag gtttaacaac ccgtaaactc gcccagaagc taggtgtaga gcagcctaca    3540
ttgtattggc atgtaaaaaa taagcgggct ttgctcgacg ccttagccat tgagatgtta    3600
gataggcacc atactcactt tgcccttta aaggggaaa gctggcaaga ttttttacgt    3660
aataacgcta aagttttag atgtgcttta ctaagtcatc gcgatggagc aaaagtacat    3720
ttaggtacac ggcctacaga aaacagtat gaaactctcg aaaatcaatt agcctttta    3780 tgccaacaag gttttcact agagaatgca ttatatgcac tcagcgcagt ggggcatttt    3840
actttaggtt gcgtattgga agatcaagag catcaagtcg ctaaagaaga agggaaaca    3900 cctactactg atagtatgcc gccattatta cgacaagcta tcgaattatt tgatcaccaa    3960
ggtgcagagc cagccttctt attcggcctt gaattgatca tatgcggatt agaaaaacaa    4020
cttaaatgtg aaagtgggtc ttaaaagcag cataaccttt ttccgtgatg gtaacttcac    4080
tagtttaaaa ggatctaggt gaagatcctt tttgataatc tcatgaccaa atccccttaa    4140
cgtgagtttt cgttccactg agcgtcagac cccgtagaaa agatcaaagg atcttcttga    4200
gatccttttt ttctgcgcgt aatctgctgc ttgcaaacaa aaaaaccacc gctaccagcg    4260
gtggtttgtt tgccggatca agagctacca actctttttc cgaaggtaac tggcttcagc    4320
agagcgcaga taccaaatac tgtccttcta gtgtagccgt agttaggcca ccacttcaag    4380
aactctgtag caccgcctac atacctcgct ctgctaatcc tgttaccagt ggctgctgcc    4440
```

```
agtggcgata agtcgtgtct taccggggttg gactcaagac gatagttacc ggataaggcg    4500
cagcggtcgg gctgaacggg gggttcgtgc acacagccca gcttggagcg aacgacctac    4560
accgaactga gatacctaca gcgtgagcta tgagaaagcg ccacgcttcc cgaagggaga    4620
aaggcggaca ggtatccggt aagcggcagg gtcggaacag gagagcgcac gagggagctt    4680
ccagggggaa acgcctggta tctttatagt cctgtcgggt ttcgccacct ctgacttgag    4740
cgtcgatttt tgtgatgctc gtcagggggg cggagcctat ggaaaaacgc cagcaacgcg    4800
gcctttttac ggttcctggc cttttgctgg ccttttgctc acatgacccg acaccatcga    4860
atggccagat gattaattcc taattttttgt tgacactcta tcattgatag agttatttta    4920
ccactcccta tcagtgatag agaaaagtga atgaatagt tcgacaaaaa t              4971
```

<210> SEQ ID NO 3
<211> LENGTH: 4765
<212> TYPE: DNA
<213> ORGANISM: Artificial Sequence
<220> FEATURE:
<223> OTHER INFORMATION: synthetic expression and cloning vector derived
      from E. coli

<400> SEQUENCE: 3

```
ctagataaga aggaagaaaa ataatgaaca ataacgatct ctttcaggca tcacgtcggc      60
gttttctggc acaactcggc ggcttaaccg tcgccgggat gctggggccg tcattgttaa     120
cgccgcgacg tgcgactgcg gcccagccgg ccatggcggg atccgttcaa ctagcagacc     180
attatcaaca aaatactcca attggcgatg gccctgtcct tttaccagac aaccattacc     240
tgtcgacaca atctgccctt tcgaaagatc ccaacgaaaa gcgtgaccac atggtccttc     300 ttgagttttgt aactgctgct gggatttccg gtggtggtgg tgctacccccg caggacctga     360 acaccatgct gggtggtggt ggtagtaaag gagaagaact tttcactgga gttgtcccaa     420
ttcttgttga attagatggt gatgttaatg gcacaaatt ttctgtcagt ggagagggtg     480
aaggtgatgc aacatacgga aaacttaccc ttaaattat ttgcactact ggaaaactac     540
ctgttccatg gccaacactt gtcactactt tctcttatgg tgttcaatgc ttttcccgtt     600
atccggatca tatgaaacgg catgactttt tcaagagtgc catgcccgaa ggttatgtac     660
aggaacgcac tatatctttc aaagatgacg ggaactacaa gacgcgtgct gaagtcaagt     720 tgaaggtga taccccttgtt aatcgtatcg agttaaaagg tattgatttt aagaagatg     780 gaaacattct cggacacaaa ctcgagtaca actataactc acacaatgta tacatcacgg     840
cagacaaaca aaagaatgga atcaaagcta acttcaaaat tcgccacaac attgaagatt     900
cggcctcggg ggccgcagaa caaaaactca tctcagaaga aatctgtat ttccagggcg     960 atgcttgcgg tggcaccgac ccctgcaag ctgaaaccga ccagctggaa gacgagaaat    1020
ccgctctgca gactgaaatc gctaacctgc tgaaagagaa agagaaactg gaattcattc    1080
tggctgctca cggcggttgt gggctaggct aataactaa gccaaggagg aaaataaat    1140 gaaatacccta ttgcctacgg cagccgctgg attgttatta ctcgcggcac agccggccat    1200
ggcaagcatc tgcggtggcc gtatcgctcg tctggaagaa aaagtaaaaaa ccctgaaagc    1260 tcagaactcc gaactggctt ccaccgctaa catgctgcgt gaacaggttg ctcagctgaa    1320
gcagaaagtt atgaaccacg gcggttgtgg tggcggttcc ctagcgggct ccggttccgg    1380
tgattttgat tatgaaaaaa tggcaaacgc taataagggg gctatgaccg aaaatgccga    1440
tgaaaacgcg ctacagtctg acgctaaagg caaacttgat tctgtcgcta ctgattacgg    1500
tgctgctatc gatggtttca ttggtgacgt ttccggcctt gctaatggta atggtgctac    1560
```

```
tggtgatttt gctggctcta attcccaaat ggctcaagtc ggtgacggtg ataattcacc    1620
tttaatgaat aatttccgtc aatatttacc ttctttgcct cagtcggttg aatgtcgccc    1680
ttatgtcttt ggcgctggta aaccatatga attttctatt gattgtgaca aaataaactt    1740
attccgtggt gtctttgcgt ttcttttata tgttgccacc tttatgtatg tattttcgac    1800
gtttgctaac atactgcgta ataaggagtc ttaataagct tgacctgtga agtgaaaaat    1860
ggcgcacatt gtgcgacatt ttttttgtct gccgtttacc gctactgcgt cacggatctc    1920
cacgcgccct gtagcggcgc attaagcgcg gcgggtgtgg tggttacgcg cagcgtgacc    1980
gctacacttg ccagcgccct agcgcccgct cctttcgctt tcttcccttc ctttctcgcc    2040
acgttcgccg gctttccccg tcaagctcta aatcggggc tccctttagg gttccgattt    2100
agtgctttac ggcacctcga ccccaaaaaa cttgattagg gtgatggttc acgtagtggg    2160
ccatcgccct gatagacggt ttttcgccct tgacgttgg agtccacgtt ctttaatagt     2220
ggactcttgt tccaaactgg aacaacactc aaccctatct cggtctattc ttttgattta    2280
taagggattt tgccgatttc ggcctattgg ttaaaaatg agctgattta caaaaattt      2340 aacgcgcatg caacgcttac aatttcaggt ggcactttc ggggaaatgt gcgcggaacc     2400
cctatttgtt tatttttcta aatacattca aatatgtatc cgctcatgag acaataaccc    2460
tgataaatgc ttcaataata ttgaaaaagg aagagtatgg agaaaaaaat cactggatat    2520
accaccgttg atatatccca atggcatcgt aaagaacatt ttgaggcatt tcagtcagtt    2580
gctcaatgta cctataacca gaccgttcag ctggatatta cggcctttt aaagaccgta     2640 aagaaaaata agcacaagtt ttatccggcc tttattcaca ttcttgcccg cctgatgaat    2700
gctcatccgg aattccgtat ggcaatgaaa gacggtgagc tggtgatatg ggatagtgtt    2760
cacccttgtt acaccgtttt ccatgagcaa actgaaacgt tttcatcgct ctggagtgaa    2820
taccacgacg atttccggca gtttctacac atatattcgc aagatgtggc gtgttacggt    2880
gaaaacctgg cctatttccc taaagggttt attgagaata tgttttcgt ctcagccaat     2940 ccctgggtga gtttcaccag ttttgattta aacgtggcca atatggacaa cttcttcgcc    3000
cccgttttca ctatgggcaa atattatacg caaggcgaca aggtgctgat gccgctggcg    3060
attcaggttc atcatgccgt ttgtgatggc ttccatgtcg gcagaatgct taatgaatta    3120
caacagtact gcgatgagtg cagggcggg gcgtaatagg aattaatgat gtctcgttta    3180
gataaaagta aagtgattaa cagcgcatta gagctgctta atgaggtcgg aatcgaaggt    3240
ttaacaaccc gtaaactcgc ccagaagcta ggtgtagagc agcctacatt gtattggcat    3300
gtaaaaaata agcgggcttt gctcgacgcc ttagccattg agatgttaga taggcaccat    3360
actcactttt gcccttaga aggggaaagc tggcaagatt ttttacgtaa taacgctaaa     3420
agttttagat gtgctttact aagtcatcgc gatggagcaa aagtacattt aggtacacgg    3480
cctacagaaa aacagtatga aactctcgaa aatcaattag ccttttatg ccaacaaggt     3540 ttttcactag agaatgcatt atatgcactc agcgcagtgg ggcattttac tttaggttgc    3600
gtattggaag atcaagagca tcaagtcgct aaagaagaaa gggaaacacc tactactgat    3660
agtatgccgc cattattacg acaagctatc gaattatttg atcaccaagg tgcagagcca    3720
gccttcttat tcggccttga attgatcata tgcggattag aaaaacaact aaatgtgaa     3780 agtgggtctt aaaagcagca taaccttttt ccgtgatggt aacttcacta ttaacgctcg    3840
gttgccgccg ggcgtttttt aatattttgt taactagttt aaaaggatct aggtgaagat    3900 ccttttttgat aatctcatga ccaaaatccc ttaacgtgag ttttcgttcc actgagcgtc    3960
```

```
agacccgta gaaaagatca aaggatcttc ttgagatcct tttttctgc gcgtaatctg    4020 ctgcttgcaa acaaaaaaac caccgctacc agcggtggtt tgtttgccgg atcaagagct    4080
accaactctt tttccgaagg taactggctt cagcagagcg cagataccaa atactgtcct    4140
tctagtgtag ccgtagttag gccaccactt caagaactct gtagcaccgc ctacatacct    4200
cgctctgcta atcctgttac cagtggctgc tgccagtggc gataagtcgt gtcttaccgg    4260
gttggactca agacgatagt taccggataa ggcgcagcgg tcgggctgaa cggggggttc    4320
gtgcacacag cccagcttgg agcgaacgac ctacaccgaa ctgagatacc tacagcgtga    4380
gctatgagaa agcgccacgc ttcccgaagg gagaaaggcg gacaggtatc cggtaagcgg    4440
cagggtcgga acaggagagc gcacgaggga gcttccaggg ggaaacgcct ggtatcttta    4500
tagtcctgtc gggtttcgcc acctctgact tgagcgtcga ttttgtgat gctcgtcagg    4560 ggggcggagc ctatggaaaa acgccagcaa cgcggccttt ttacggttcc tggccttttg    4620
ctggcctttt gctcacatga cccgacacca tcgaatggcc agatgattaa ttcctaattt    4680
ttgttgacac tctatcattg atagagttat ttaccactc cctatcagtg atagagaaaa    4740
gtgaaatgaa tagttcgaca aaaat    4765

<210> SEQ ID NO 4
<211> LENGTH: 823
<212> TYPE: DNA
<213> ORGANISM: Artificial Sequence
<220> FEATURE:
<223> OTHER INFORMATION: cloning cassette containing synthetic gene
      derived from E. coli

<400> SEQUENCE: 4
ggcccagccg gccatggctc acccagaaac gctggtgaaa gtaaagatg ctgaagatca    60 gttgggtgca cgagtgggtt acatcgaact ggatctcaac agcggtaaga tccttgagag    120
ttttcgcccc gaagaacgtt ttccaatgat gagcactttt aaagttctgc tatgtggcgc    180
ggtattatcc cgtattgacg ccgggcaaga gcaactcggt cgccgcatac actattctca    240
gaatgacttg gttgagtact caccagtcac agaaaagcat cttacggatg gcatgacagt    300
aagagaatta tgcagtgctg ccataaccat gagtgataac actgcggcca acttacttct    360
gacaacgatc ggaggaccga aggagctaac cgcttttttg cacaacatgg gggatcatgt    420
aactcgcctt gatcgttggg aaccggagct gaatgaagcc ataccaaacg acgagcgtga    480
caccacgatg cctgtagcaa tggcaacaac gttgcgcaaa ctattaactg gcgaactact    540
tactctagct tcccggcaac aattgataga ctggatggag gcggataaag ttgcaggacc    600
acttctgcgc tcggcccttc cggctggctg gtttattgct gataaatctg gagccggtga    660
gcgtggctct cgcggtatca ttgcagcact ggggccagat ggtaagccct cccgtatcgt    720
agttatctac acgacgggga gtcaggcaac tatggatgaa cgaaatagac agatcgctga    780
gataggtgcc tcactgatta agcattggtc ggcctcgggg gcc    823

<210> SEQ ID NO 5
<211> LENGTH: 7
<212> TYPE: PRT
<213> ORGANISM: Escherichia coli
<220> FEATURE:
<221> NAME/KEY: MISC_FEATURE
<222> LOCATION: (1)..(1)
<223> OTHER INFORMATION: X = S or T
<220> FEATURE:
<221> NAME/KEY: MISC_FEATURE
<222> LOCATION: (4)..(4)
```

```
<223> OTHER INFORMATION: X = any amino acid

<400> SEQUENCE: 5

Xaa Arg Arg Xaa Phe Leu Lys
1               5

<210> SEQ ID NO 6
<211> LENGTH: 5
<212> TYPE: PRT
<213> ORGANISM: Escherichia coli
<220> FEATURE:
<221> NAME/KEY: MISC_FEATURE
<222> LOCATION: (3)..(3)
<223> OTHER INFORMATION: X = any amino acid
<220> FEATURE:
<221> NAME/KEY: MISC_FEATURE
<222> LOCATION: (4)..(5)
<223> OTHER INFORMATION: X = any hydrophobic amino acid

<400> SEQUENCE: 6

Arg Arg Xaa Xaa Xaa
1               5

<210> SEQ ID NO 7
<211> LENGTH: 37
<212> TYPE: PRT
<213> ORGANISM: Escherichia coli

<400> SEQUENCE: 7

Met Asn Asn Asn Asp Leu Phe Gln Ala Arg Arg Arg Phe Leu Ala Gln
1               5                   10                  15

Leu Gly Gly Leu Thr Val Ala Gly Met Leu Gly Pro Ser Leu Leu Thr
            20                  25                  30

Arg Arg Ala Thr Ala
        35

<210> SEQ ID NO 8
<211> LENGTH: 54
<212> TYPE: DNA
<213> ORGANISM: Escherichia coli

<400> SEQUENCE: 8
atgaacaata acgatctctt tcaggcatca cgtcggttcc tggcacaact cggc          54

<210> SEQ ID NO 9
<211> LENGTH: 54
<212> TYPE: DNA
<213> ORGANISM: Escherichia coli

<400> SEQUENCE: 9
tacttgttat tgctagagaa agtccgtagt gcagccaagg accgtgttga gccg          54

<210> SEQ ID NO 10
<211> LENGTH: 41
<212> TYPE: DNA
<213> ORGANISM: Escherichia coli

<400> SEQUENCE: 10
gtcgccggga tgctggggcc gtcattgtta acgccgcgac g                       41

<210> SEQ ID NO 11
<211> LENGTH: 38
<212> TYPE: DNA
<213> ORGANISM: Escherichia coli
```

```
<400> SEQUENCE: 11
cagcggccct acgaccccgg cagtaacaat tgcgctgc                          38
```